United States Patent [19]
Chaudhary et al.

[11] Patent Number: 5,464,753
[45] Date of Patent: Nov. 7, 1995

[54] PURIFICATION AND MANIPULATION OF BONE MARROW AND BLOOD CELLS ON THE BASIS OF P-GLYCOPROTEIN EXPRESSION

[76] Inventors: Preet M. Chaudhary, 809 S. Damen, #1107B, Chicago, Ill. 60612; Igor B. Roninson, 818 S. Laflin, Chicago, Ill. 60607

[21] Appl. No.: 128,056

[22] Filed: Sep. 28, 1993

Related U.S. Application Data

[63] Continuation of Ser. No. 666,340, Mar. 8, 1991, abandoned.
[51] Int. Cl.[6] .................... G01N 33/49; G01N 33/533; G01N 33/536
[52] U.S. Cl. .................... 435/7.24; 435/2; 435/7.21; 435/240.2; 436/56; 436/172; 436/536
[58] Field of Search ............... 435/2, 7.24, 7.21, 435/240.2; 436/536, 56, 172

[56] References Cited

U.S. PATENT DOCUMENTS 5,061,620 10/1991 Tsukamoto et al. .................. 435/7.21

OTHER PUBLICATIONS

Srour et al. "Simultaneous use of CD34, CD15, anti-HLA-DR and rhodamine 123 for the isolation of precursors of human hematopoietic progenitor cells", Exp. Hematol. vol. 18, p. 549, Abstract #3, 1990.
Efferth et al, "Reciprocal Correlation Between Expression of P-Glycoprotein and accumulation of Rhodamine 123 in Human Tumors", Anticancer Research vol. 9, pp. 1633–1638, 1989.
Ploemacher et al, "Cells With Marrow and Spleen Repopulation Ability and Forming Spleen Colonies on Day 16, 12 and 8 Are Sequentially Ordered on the Basis of Increasing Rhodamine 123 Retention", Journal of Cellular Physiology, vol. 136, pp. 531–536, 1988.
Neyfakh et al., "Multidrug–Resistance Phenotype of a Subpopulation of T–Lymphocytes without Drug Selection", Experimental Cell Research, vol. 185, pp. 496–505, 1989.
DAKO bulletin, "The CD System", 1989.
Ball et al, "Correlation of CD34 and Multidrug Resistance P170 with Fab and Cytogenetics but not Prognosis in Acute Myeloid Leukemia (AML)", Blood, vol. 76 (10, Suppl 1), p. 252a, 1990.
Mulder et al, "Separation and Functional Analysis of Bone Marrow Cells Separated by Rhodamine–123 Fluorescence", Exp. Hematol, vol. 15, pp. 99–104, 1987.
Bertoncello et al, "Multiparameter Analysis of Transplantable Hemopoietic Stem Cells: 1. The Separation and Enrichment of Stem Cells Homing to Marrow and Spleen on the Basis of Rhodamine–123 Fluorescence", Exp. Hematol. vol. 13, pp. 999–1006, 1985.
van der Bliek et al., "Multi Drug Resistance", Advances in Cancer Research 52:165 1989.
Neyfakh 1988. "Use of Fluorescent Dyes as Molecular Probes for the Study of Multidrug Resistance", Exp. Cell Res. 174:168–176.
Hamada et al., "Mouse–Human Chimeric Antibody against the Multidrug Transporter P–Glycoprotein", Jun. 1990. Cancer Res 50:3167.

*Primary Examiner*—Toni R. Scheiner
*Assistant Examiner*—Nancy J. Parsons
*Attorney, Agent, or Firm*—Banner & Allegretti

[57] ABSTRACT

The invention provides methods for purifying or manipulating bone marrow and blood cells based upon P-glycoprotein expression. The methods rely upon immunopurification procedures or upon differential accumulation of materials subject to P-glycoprotein mediated efflux.

8 Claims, No Drawings

PURIFICATION AND MANIPULATION OF BONE MARROW AND BLOOD CELLS ON THE BASIS OF P-GLYCOPROTEIN EXPRESSION

This application is a continuation of application Ser. No. 07/666,340, filed Mar. 8, 1991, now abandoned.

BACKGROUND OF THE INVENTION

1. Field of the Invention

The invention relates to methods for purification and manipulation of hemopoietic progenitor cells and lymphocytes. More particularly, the invention relates to methods for identifying, manipulating and purifying pluripotent hemopoietic stem cells (PHSC) and certain lymphocytic types to provide or increase populations of such cells for a variety of therapeutic and research purposes.

2. Summary of the Related Art

Pluripotent hemopoietic stem cells (PHSC) comprise less than about 1% of total bone marrow cells, and are self-renewing cells that give rise to all the different types of blood cells. Research directed toward isolation and characterization of PHSC has a history of over 20 years.

Visser et al., Exp. Hematol. 18:248–256 (1990), reviews research concerning purification of PHSC, including partial purification strategies used to avoid graft-versus-host disease in heterologous bone marrow transplantation and to remove malignant cells from bone marrow for autologous transplantation.

Various methods have been developed to assay PHSC. For example, Sutherland et al., Proc. Natl. Acad. Sci. USA 87: 3584–3588 (1990), discloses an assay ("long term culture (LTC) initiating cell assay") for PHSC using measurement of ability to give rise to short-term colony forming cells five to eight weeks after overlay on an irradiated stromal layer.

Methods of purifying PHSC based on immunological techniques involving surface antigens are known in the art. Sutherland, et al., Blood 74:1563–1570 (1990), discloses an immunological method which provides about 800-fold enrichment of PHSC and utilizes, inter alia, the fact that PHSC express the CD34 antigen, which is otherwise expressed only by clonogenic cells at a lower level.

Purification of PHSC based on differential rhodamine 123 (Rh) accumulation is also known in the art. Bartoncello et al., Exp. Hematol. 13:999–1006 (1985), discloses a method for enriching PHSC, using fluorescence-activated cell sorting (FACS) to separate the Rh-dull PHSC from the Rh-bright remaining cells. Srour et al., Exp. Hematol. 18:549 (1990) teaches that PHSC are an Rh-dull subset of CD34-expressing cells.

Reduced accumulation of Rh has been attributed to the expression of P-glycoprotein, a multidrug transporter, in some cell types, but has been attributed to reduced numbers or activity of mitochondria in PHSC.

Neyfakh et al., Exp. Cell Res. 174:168–176 (1988), discloses that multidrug resistant hamster fibroblasts accumulate lower concentrations of fluorescent dyes, including Rh, than do their drug-sensitive counterparts, and concludes that this difference results from increased efflux of fluorescent dyes from the multi drug-resistant cells. Neyfakh et al., Exp. Cell. Res. 185:496–505 (1989), teaches that multidrug resistance in B-lymphoma cell lines and T-lymphocytes is inversely proportional to accumulation of fluorescent dyes, including Rh, that there are normal mouse T-lymphocytes that demonstrate rapid efflux of Rh which can be prevented by inhibitors of the multidrug transporter system, and that an Rh-effluxing T-lymphoma contained high levels of P-glycoprotein mRNA. In contrast, McCarthy et al., I. J. Cell Cloning 8:184–195 (1990), teaches that decreased Rh accumulation in PHSC results from a reduced number of Rh-accumulating mitochondria in these quiescent cells. See also Spangrude et al., Proc. Natl. Acad. Sci. USA 87:7433–7437 (1990).

Thus there are currently at least two available methods for enriching for PHSC. Each of these available methods has limitations, however. Enrichment based on CD34 recognition by antibodies cannot fully purify PHSC, since other cells also express CD34. Enrichment based on FACS separation of rhodamine-dull cells also imperfectly purifies PHSC and is not readily amenable to multi-parameter FACS analysis due to the overlap between the fluorescent signal produced by rhodamine and those produced by other probes.

There is, therefore, a need for additional methods for purifying PHSC which may be separately used, in conjunction with each other, or in conjunction with existing methods to effect better purification of PHSC than is presently available. Such methods may be based upon antibody recognition or upon differential accumulation of molecules between PHSC and other cell types.

BRIEF SUMMARY OF THE INVENTION

The invention relates to methods for the purification or enrichment of pluripotent hemopoietic stem cells (PHSC) and certain subsets of lymphocytes. The invention provides methods for such purification which are additional to, and in some aspects superior to available methods for such purification. The invention derives, in significant degree, from the discovery that PHSC, more than most other cell types found in bone marrow or blood, express significant levels of P-glycoprotein. This discovery has enabled the development of procedures for purifying PHSC and certain lymphocyte types by using antibodies to P-glycoprotein in immuno-purification schemes, as well as by using procedures based on differential accumulation of molecules which are pumped out of cells by P-glycoprotein. The latter type of method can utilize fluorescent dyes and enrichment by FACS, or it can utilize cytotoxic compounds to select against cells other than PHSC or P-glycoprotein-expressing lymphocytes. The invention specifically contemplates the use of one or more of the above-identified procedures in conjunction with negative selection directed against other cell types.

An object of the invention is to provide methods for purifying PHSC, using in at least one step the characteristic P-glycoprotein expression by PHSC as a means of separating or selecting PHSC from other cell types.

The invention also derives in part from the discovery that certain types of peripheral blood lymphocytes (PBL) express P-glycoprotein, whereas other types do not. Thus the invention allows for the purification of or selection for certain types of lymphocytes in a manner that is useful for both therapeutic and scientific procedures. For these purposes, the invention encompasses purification and selection methods that include a step which relies upon a lymphocytic cell type having the characteristic of P-glycoprotein expression, as a means of purifying, or selecting for or against that lymphocytic cell type.

Specific preferred embodiments of the invention will become apparent from the following detailed description, examples and claims.

DETAILED DESCRIPTION OF THE SPECIFIC EMBODIMENTS

The invention relates to methods for purifying or selecting pluripotent hemopoietic stem cells (PHSC) and for purifying or selecting for or against certain lymphocyte cell types. In the methods according to the invention, particular types of cells may be separated or purified from other types of cells on the basis that only certain cell types express P-glycoprotein. Alternatively, or in addition to such separation or purification, the methods of the invention provide for the enrichment or selection of certain cell types on the basis that P-glycoprotein expression occurs only in specific cell types. The methods of the invention may include additional positive selection or purification steps or procedures based on other known characteristics of the cell type to be selected or purified. They may also include any negative selection or separation steps for the purpose of excluding or reducing the presence of other cell types. The methods of the invention will include in vivo cell enrichment or cell depletion procedures designed to increase, reduce or eliminate a particular cell type in a patient or an animal. All of these procedures will be made possible by the discovery that these certain cell types express P-glycoprotein, whereas other blood cell or blood precursor cell types do not.

The particular discoveries that make the invention possible are: (1) PHSC express P-glycoprotein; and (2) $CD8^+$ lymphocytes and $CD45RA^{++}$ T-lymphocytes express P-glycoprotein, but B lymphocytes and $CD45RO^{++}$ T-lymphocytes do not.

In a first aspect, the invention provides a method for purifying or enriching PHSC and certain lymphocytic cell types based upon P-glycoprotein-mediated efflux of fluorescent compounds. P-glycoprotein mediates efflux of compounds such as rhodamine-123, $DiOC_2(3)$, HIDC-iodide and DODC-iodide. Suitable fluorescent compounds according to the invention include these compounds, as well as any other fluorescent compounds that are characterized by having the ability to enter cells and be retained therein, by having absorbance and emission spectra that are suitable for fluorescence-activated cell sorting (FACS), and by being substrates for P-glycoprotein-mediated efflux. Such compounds are readily identified by staining and allowing time for efflux, along with comparing fluorescence before and after efflux, examining sensitivity of efflux to inhibitors of P-glycoprotein function, such as verapamil, and/or correlating fluorescence with P-glycoprotein expression based on protein (antibody) or RNA analysis. Suitable fluorescent compounds are used to stain a mixed population of cells which include a cell type that expresses P-glycoprotein. The cells are then removed to media that does not contain the compound, thereby providing an opportunity for P-glycoprotein-expressing cells to actively efflux the compound. Upon exposure to light of the appropriate excitation spectrum, cells that have extruded the compound will be "dull" and cells that have not will be "bright". Conventional FACS methodologies can then be used to separate "bright" cells from "dull" cells.

In another aspect the invention provides methods for purifying, enriching or selecting for or against PHSC or certain lymphocytic cell types using antibodies to P-glycoprotein. Antibodies to P-glycoprotein can be allowed to bind to cells expressing P-glycoprotein, then cells having bound antibody may be separated or removed from cells without bound antibody by any of a variety of conventional immunological techniques. Such techniques include FACS, immunomagnetic beads, affinity chromatography, panning and complement fixation. Purification methods according to the invention may be used in conjunction with other purification steps or methods based upon other known properties of the cell type to be purified. These additional steps or methods may be positive or negative selective steps or methods. An example of a positive step that can be used in conjunction with a P-glycoprotein-based step for purifying PHSC is any immunopurification procedure using antibodies against the CD34 surface antigen. An example of a negative step that can be used in conjunction with a P-glycoprotein-based step for purifying PHSC is to use antibodies against other cell types, e.g., anti-CD33 antibody or anti-T cell receptor antibody to remove or destroy the other cell types. Obviously, antibody-mediated positive or negative steps can be used in conjunction with P-glycoprotein-based purification steps to purify any P-glycoprotein-expressing cell type from any other cell type, so long as antibodies are available which are specific for the P-glycoprotein cell type, or for cell types other than the P-glycoprotein expressing cell type.

In another aspect, the invention provides a method for selecting or enriching PHSC or certain lymphocytic cell types based on the resistance to cytotoxic compounds conferred upon such cells by virtue of expressing P-glycoprotein. Such selection may be carried out either in vitro or in vivo by administration of the cytotoxic compounds. Since many of these cytotoxic compounds are clinically characterized drugs, it is possible to use these cytotoxic compounds in therapeutic approaches designed to increase the relative abundance of PHSC or certain lymphocytic cell types in relation to other cell types which do not express P-glycoprotein. An example of such an approach is the use of cytotoxic compounds to purge the bone marrow of tumor cells. Since many tumors do not express P-glycoprotein, bone marrow could be purged of such tumor cells by treatment with cytotoxic compounds subject to P-glycoprotein-mediated efflux. Cytotoxic compound-based selection against $CD45RO^+$ "memory" T cells, which do not express P-glycoprotein, in favor of $CD45RA^+$ "virgin" T-cells that do express P-glycoprotein provides promise for auto-immune disorders in which "memory" T cells are increased such as Graves disease, multiple sclerosis and rheumatoid arthritis. Additionally, such methods may be useful for controlling graft rejection in organ transplantation cases by using cytotoxic compounds to select against "memory" T cells.

The invention further contemplates that P-glycoprotein in PHSC may be important for PHSC function. Therefore inhibitors of P-glycoprotein function may affect proliferation or differentiation of PHSC in a manner that can be used to manipulate the composition of blood cell populations in patients for the treatment of various disease conditions. Examples of useful inhibitors include, but are not limited to, verapamil, reserpine, and cyclosporin A.

The following examples are intended to further illustrate the invention and are not limiting in nature.

EXAMPLE 1

Rh-dullness Resulting from P-glycoprotein Expression

K562 cells, which do not normally express P-glycoprotein, were repeatedly exposed to media containing recombinant retrovirus, LMDR1L6, carrying the human MDR1 (P-glycoprotein) cDNA and subsequently subcloned. The infected clones expressing P-glycoprotein, as judged by staining with a monoclonal antibody (MRK16) directed against it, were selected for further study. Both the infected and the uninfected cells were stained with Rh and then incubated in Rh-free media. Rh accumulation was analyzed using a fluorescence-activated cell sorter (FACS). Infected cells appeared Rh-dull since they had pumped out Rh, whereas the uninfected cells stained brightly with Rh. However, if verapamil (an inhibitor of P-glycoprotein) was added during the incubation step, both cell types stained brightly with Rh. This experiment demonstrates that expression of P-glycoprotein in a hemopoietic cell can make a cell appear Rh-dull. The same result was obtained with other fluorescent dyes, daunomycin (an anticancer drug which preferentially binds to DNA), $DiOC_2(3)$, HIDC iodide and DODC-iodide that stain mitochondria.

EXAMPLE 2

Efflux-mediated Rh-dullness in Mouse Bone Marrow Cells

Mouse bone marrow cells, maintained in long-term culture, were stained with Rh and then resuspended in Rh-free medium and analyzed by FACS either immediately or after 2–3 hours. No Rh-dull cells were found in the marrow if the cells were analyzed immediately. Rh-dull cells appeared only after 2–3 hours of incubation in Rh-free medium. Moreover, if the cells were incubated in the presence of verapamil, no Rh-dull cells could be observed even after 2–3 hours of incubation. This result indicates that Rh staining of bone marrow is determined by efflux rather than the initial accumulation and therefore is not related to the mitochondrial activity level of the cells.

Alternatively, mouse bone marrow cells grown in long-term culture were stained with Rh and immediately sorted into Rh-bright (upper 10–15%) and Rh-dull (lower 70–80%) fractions. Both fractions were incubated in Rh-free medium for 3–4 hours so as to allow them to efflux Rh and again analyzed by FACS. A majority of the cells that appeared to be Rh-dull after efflux were found in the fraction that initially stained brightly with Rh. Moreover, it was found that the percentage of Rh-dull cells increased with the time allowed for efflux. These results further support the conclusion that Rh-dull nature of some of the cells in the bone marrow is determined by efflux rather than lack of active mitochondria.

EXAMPLE 3

Efflux-mediated Rh-dullness in Human Lymphoid and Blastoid Cells

Mononuclear cells of human bone marrow, obtained from a surgical sample of bone, were stained with Rh and then incubated overnight in Rh-free medium in the absence or presence of various inhibitors of P-glycoprotein. In the subsequent FACS analysis, the cells were subdivided into lymphoid and blastoid populations (as determined by size and granularity) for comparison with previous reports that the lymphoid population contains all or most PHSC. We have found that 60–65% of cells in the lymphoid population were Rh-dull, if allowed to efflux in the absence of inhibitors of P-glycoprotein. Twenty to thirty percent of cells in the blast region were also found to be Rh-dull. In contrast, all cells that were incubated in the presence of P-glycoprotein inhibitors were found to be Rh-bright. Essentially similar results were obtained with daunomycin and $DiOC_2(3)$.

EXAMPLE 4

Correlation Between Efflux-mediated Rh-Dullness and P-glycoprotein Antigenicity Bone marrow cells were stained with Rh and, after overnight efflux, labeled by indirect immunofluorescence with MRK16, a monoclonal antibody directed against P-glycoprotein. MRK16 antibody is available upon request from Takashi Tsuruo at the Tokyo University. See Hamada and Tsuruo, Proc. Natl. Acad. Sci. USA 73:7785–7789 (1976). It was found that all the Rh-dull cells were MRK16$^+$ and all the Rh-bright cells were MRK16$^-$. Moreover, there was an inverse correlation between the amount of antibody staining and the degree of Rh retention. Similar results were obtained if the cells were labeled with $DiOC_2(3)$ or DODC-iodide instead of Rh.

EXAMPLE 5

Correlation Between Efflux-Mediated Rh-Dullness and CD34 Antigenicity

Bone marrow cells were stained with Rh and, after incubation in Rh-free medium, with or without verapamil, were stained with an anti-CD34 antibody (HPCA-1). It was found that almost all the CD34$^+$ cells were Rh-dull, if allowed to efflux Rh in the absence of verapamil. Some cells were found to be more Rh-dull than the others. However, if verapamil was present during the efflux period, all the cells stained brightly with Rh. This indicates that the Rh-dull nature of CD34$^+$ cells is due to efflux rather than lack of mitochondrial activity, as previously postulated.

The above experiment was repeated with $DiOC_2(3)$ instead of Rh. A positive correlation was found between the expression of CD34 antigen and the efflux of $DiOC_2(3)$ so that the highest CD34 expressing cells had the lowest $DiOC_2(3)$ staining of the CD34$^+$ population. Similar results were obtained when HIDC-iodide or DODC-iodide were used in place of $DiOC_2(3)$.

EXAMPLE 6

Correlation Between P-glycoprotein and CD34 Antigenicity

Bone marrow cells were analyzed by double-labeling with both MRK16 and anti-CD34 antibodies. It was found that at least a portion of the CD34$^+$ cells were highly MRK16$^+$; there appears to be a positive correlation between the expression of CD34 and P-glycoprotein.

EXAMPLE 7

Low Level HLA-DR Expression in CD34 and P-glycoprotein Expressing Cells

To examine the HLA-DR status of the CD34$^+$ and P-glycoprotein expressing cells a three-color labeling experiment was performed on the lymphoid population. For this experiment, DODC-iodide was used in place of Rh as a substrate for P-glycoprotein. There was a progressive decline in the HLA-DR expression as the CD34 expression increased. Similarly, there was a progressive decline in the DODC-iodide fluorescence as the CD34 expression increased. When only the highest 10% of CD34-expressing cells were analyzed for the expression of HLA-DR and DODC-iodide staining, almost all of them were found to have low HLA-DR expression and low DODC-iodide staining. Similar results were obtained when HIDC-iodide was used in place of DODC-iodide. Thus, P-glycoprotein-mediated efflux of fluorescent dyes shows a positive correlation with the expression of CD34 and with low levels expression of the HLA-DR antigen, which is in agreement with the known characteristics of PHSC.

EXAMPLE 8

Inverse Correlation Between Either Efflux-mediated Dullness or CD34 Antigenicity and CD33 Antigenicity The experiment described in Example 7 was repeated with anti-CD33 antibody in place of anti-HLA-DR antibody. Almost all the CD33$^+$ cells stained brightly with HIDC-iodide indicating that they express very little or no P-glycoprotein. All the CD34$^+$, HIDC-iodide effluxing cells were found to be CD33$^-$. The same result was obtained when DODC-iodide was used in place of HIDC-iodide. These results are in agreement with the previously known fact that the PHSC are CD34$^+$ and CD33$^-$.

EXAMPLE 9

Colony Formation by Lymphoid Cells Separated by Rh-FACS

Bone marrow cells from a human lymphoid population were sorted after overnight Rh efflux into Rh-dull and Rh-bright fractions, and 10,000 cells of each type were put in colony forming assays in the presence of various growth factors. Colonies were counted after 14 days. The distribution of various colonies is shown in Table 1 below.

TABLE 1

| | Number of Colonies per 10,000 cells | |
|---|---|---|
| | Rh-dull | Rh-bright |
| Erythroid | 66 | 1 |
| CFU-G (Granulocytic) | 27 | 0 |
| CFU-M (macrophage) | 32 | 1 |
| CFU-GM | 22 | 0 |
| CFU-Mix | 9 | 0 |
| TOTAL | 156 | 2 |

EXAMPLE 10

Colony Formation by Blastoid Cells Separated by Rh-FACS

The experiment described in Example 9 was repeated with human cells from the blast region and the results are shown in Table 2 below.

TABLE 2

| | Number of Colonies per 15,000 cells | |
|---|---|---|
| | Rh-dull | Rh-bright |
| Erythroid | 130 | 7 |
| CFU-G | 27 | 0 |
| CFU-M | 43 | 8 |
| CFU-GM | 62 | 3 |
| CFU-Mix | 18 | 0 |
| TOTAL | 291 | 18 |

EXAMPLE 11

Colony Formation by Lymphoid Cells Separated by Anti-P-glycoprotein FACS

Cells from the lymphoid region were sorted into MRK 16$^+$ and MRK 16$^-$ fractions by incubation with MRK 16 antibody followed by incubation with FITC-conjugated sheep anti-mouse antibody and FACS. Fractions were then tested and assayed for colony forming ability. The results are shown in Table 3 below.

TABLE 3

| | Number of Colonies per 28,000 cells | |
|---|---|---|
| | MRK 16$^+$ | MRK16$^-$ |
| Erythroid | 70 | 2 |
| CFU-G | 20 | 0 |
| CFU-M | 13 | 1 |
| CFU-GM | 12 | 1 |
| CFU-Mix | 5 | 0 |
| TOTAL | 120 | 4 |

EXAMPLE 12

LTC-initiating Cells Separated by Rh-FACS

Cells from the lymphoid region were sorted into Rh-dull and Rh-bright fractions and 10$^5$ cells were put on pre-irradiated stromal layers in triplicate, to assay for LTC-initiating cells. After one week, one half of the non-adherent cells were collected from each LTC and assayed for clonogenic cells. The results are shown in Tables 4 and 5 below.

TABLE 4

| | Number of Colonies per 2 × 10$^5$ Cells at the time of Establishing the Long Term Culture | |
|---|---|---|
| | Rh-dull | Rh-bright |
| Erythroid | 179 | 10 |
| CFU-G | 28 | 4 |
| CFU-M | 59 | 7 |
| CFU-GM | 56 | 3 |
| CFU-Mix | 13 | 0 |
| TOTAL | 335 | 24 |

TABLE 5

| | Number of Colonies Per One Half of Non-Adherent Cells at Different Time Points | |
|---|---|---|
| | Rh-dull | Rh-bright |
| 1st week | 451 | 4 |
| 2nd week | 87 | 0 |
| 3rd week | 51 | 0 |
| 4th week | 31 | 0 |
| 5th week | 20 | 0 |

EXAMPLE 13

LTC-initiating Cells Separated by Anti-P-glycoprotein FACS

The experiment described in Example 12 was repeated on cells sorted on the basis of MRK-16 staining and 4×10⁴ cells were put in LTC in duplicate. After one week, one half of the nonadherent cells were collected from each LTC and assayed for clonogenic cells. The results are shown in Tables 6 and 7 below.

TABLE 6

Number of Total Colonies per $4 \times 10^3$ Cells at the time of establishing the long term culture

| MRK 16⁺ | MRK 16⁻ |
|---------|---------|
| 76      | 0       |

TABLE 7

Number of colonies per one half of non-adherent cells at different time points

|          | MRK 16⁺ | MRK 16⁻ |
|----------|---------|---------|
| 1st week | 22      | 0       |
| 2nd week | 38      | 0       |
| 3rd week | 16      | 0       |
| 4th week | 8       | 0       |
| 5th week | 12      | 0       |

EXAMPLE 14

Peripheral blood lymphocytes (PBL) were isolated from human peripheral blood according to standard procedures. Rh efflux was analyzed as described in Example 2. Forty to 60% of PBL were found to efflux Rh, in a manner which was completely inhibited by verapamil.

EXAMPLE 15

Correlation Between Rh-dullness and P-glycoprotein Antigenicity in PBL

PBL were stained with Rh and after overnight efflux, labelled by indirect immunofluorescence with MRK 16, as described in Example 4. Rh-dull cells stained brightly with MRK 16, whereas Rh-bright cells did not stain with MRK 16. Similar results were obtained when DiOC₂ was used instead of Rh.

EXAMPLE 16

Rh-efflux by Various Subsets of PBL

PBL were stained with Rh and after overnight efflux, labelled by indirect immunofluorescence with antibodies against antigens found on specific subsets of PBL. The antibodies used in this study recognized B-lymphocyte-specific antigens, CD8 (cytotoxic/suppressor T cell antigen), CD4 (helper T cell antigen), CD45RA (virgin T cell antigen) or CD45RO (memory T cell antigen). The results of these experiments are shown in Table 8 below.

TABLE 8

Correlation of Rh-dullness with Various Surface Antigens on PBL

| PBL Surface Antigen  | Rh-dullness |
|----------------------|-------------|
| B cell antigen       | −           |
| CD8                  | +           |
| CD4                  | ±           |
| CD45RA (high levels) | +           |
| CD45RO (high levels) | −           |

+ = >80% are Rh dull
± = 40–60% are Rh dull
− = <30% are Rh dull

EXAMPLE 17

Conditions for Dye Efflux Studies

Except where indicated to the contrary, the conditions used for dye efflux studies were essentially the following.

Rhodamine-123 was obtained from Kodak (Rochester, N.Y.). DODC-iodide, HIDC-iodide, daunomycin, verapamil and reserpine were obtained from Sigma (St. Louis, Mo.). DiOC₂(3) was obtained from Molecular Probes (Eugene, Oreg.).

For Rh-123 staining, cells were suspended at 2×10⁵ cells/ml in 5 ml of media containing 1 µg/ml of Rh-123 for 5 minutes at 37° C. Cells were washed twice in rhodamine-free media and resuspended in dye-free media in the presence or absence of 30 µM verapamil. Cells were incubated for 1.5 hours in humidified atmosphere in the presence of 7% CO₂ at 37° C. After the incubation, cells were pelleted by centrifugation and resuspended in 0.5 ml of media containing 0.15 mg/ml of propidium iodide and kept on ice until flow cytometric analysis. A similar procedure was used for studies with other fluorescent dyes except no propidium iodide was added for daunomycin, HIDC-iodide and DODC-iodide.

Human bone marrow was obtained from surgical bone samples or from marrow aspirates. Low density mononuclear cells were isolated by density centrifugation in Histopaque-1077® (Sigma, St. Louis, Mo.). Cells were either used fresh or stored at −70° C. in the presence of 10% DMSO until use. Dye efflux in bone marrow cells was studied in essentially the same way as in K562 cells except that the cells were allowed in some cases to efflux the dyes overnight and lower dye concentrations were used when cells were to be subsequently labeled by immunofluorescence.

EXAMPLE 18

Conditions for Immunofluorescence Assays

Except where indicated to the contrary, the conditions used for immunofluorescence studies were essentially the following.

Mouse monoclonal antibodies against CD34 (HPCA-1; IgG₁ isotype), CD33 (PE conjugate; IgG₁) and HLA-DR (PE conjugate; IgG₂ₐ) and their isotype controls were obtained from Becton Dickinson, San Jose, Calif. CD34 (FITC conjugate) was obtained from AMAC, Inc., Westbrook, Me. MRK16 monoclonal antibody against P-glycoprotein (IgG₂ₐ) was obtained from Dr. Takashi Tsuruo (Tokyo University). PE-conjugated Goat anti-mouse IgG1 and IgG2a were obtained from Fisher Biotech (Fairlawn,

N.J.).

For double labeling with HPCA-1 and Rh-123, cells were labeled with 100 ng/ml of Rh-123 and allowed to efflux the dye overnight at 37° C. and 7% $CO_2$ in the absence or presence of verapamil, as described above. Cells were then labeled with 20 μl of HPCA-1 or the isotype control, washed twice with ice cold PBS containing 2% FCS and then labeled with Texas-red conjugated goat anti-mouse IgG. Cells were then washed twice and kept on ice until analysis. Controls consisting of cells stained with either Rh-123 or HPCA-1 alone were used to determine the optimal voltage and gain settings on the flow cytometer. Cells were maintained at 4° C. during all the steps of antibody labeling, including centrifugation between the washes. Each incubation step was for 30 minutes.

Essentially the same protocol was used for double labeling with $DiOC_2$ and HPCA-1 with the following modifications. Cells were labeled with 30 ng/ml of $DiOC_2$ for 10 minutes and allowed to efflux the dye for only two hours in the dye-free media. PE conjugated F (ab')$_2$ fragment of sheep anti-mouse IgG was used in place of the Texas-red conjugate.

For double labeling with Rh-123 and MRK16, cells were allowed to efflux Rh-123 for two hours and then incubated with the antibody at a concentration of 10 μg/$10^6$ cells. After two washes, cells were incubated with 10 μl of PE conjugated F(ab')$_2$ fragment of sheep anti-mouse IgG (Sigma) diluted 1:2 with 1% fetal calf serum in PBS. In some experiments 10 μl of PE-conjugated goat anti-mouse IgG2a was used in place of PE-conjugated F(ab')$_2$ fragment of sheep anti-mouse IgG. Cells were washed twice and kept on ice until analysis. The use of the high concentration of secondary antibody was critical for successful labeling. Essentially the same protocol was used when cells were stained with $DiOC_2$, HIDC-iodide, or DODC-iodide in place of Rh-123.

For double labeling with MRK16 and anti-CD34 antibody, cells were first labeled with the MRK16 antibody, washed twice, then the PE-conjugated F(ab')$_2$ fragment of sheep anti-mouse IgG was added. Mouse myeloma proteins were then added to block any free active sites on the second-step reagents, after which the FITC-conjugated anti-CD34 antibody was added. Appropriate controls consisting of cells labeled with individual antibodies were prepared. Three further controls consisting of MRK16 indirectly labeled with PE plus FITC-conjugated mouse $IgG_1$, mouse $IgG_{2a}$ indirectly labeled with PE plus FITC-conjugated mouse $IgG_1$, and mouse $IgG_{2a}$ indirectly labeled with PE plus FITC-conjugated anti-CD34 antibody were prepared to rule out any binding of PE-conjugated sheep anti-mouse antibody to anti-CD34 antibody.

For triple labeling experiments, cells were loaded with 60 ng/ml of DODC-iodide for 10 minutes in 5 ml total volume and, after two washes in dye-free media, incubated overnight (8–10 hours) in dye-free media as described above. Cells were then labeled with 20 μl of FITC-conjugated anti-CD34 antibody and 20 μl of PE-conjugated anti-HLA-DR or anti-CD33 antibodies or their corresponding isotype controls. Essentially the same conditions were used, except that HIDC-iodide replaced DODC-iodide.

EXAMPLE 19

Assays for Hematopoietic Progenitor Cells

Conditions for hematopoietic progenitor cell assays were essentially the following.

For the short-term clonogenic assay, cells were suspended in 35 mm plastic tissue culture dishes containing 1 ml mixtures of IMDM, 0.8% methylcellulose, 30% fetal calf serum, 1% bovine serum albumin, $10^{-4}$M 2-mercaptoethanol, 5 units/ml erythropoietin, 5% PHA-LCM and 10% 5637 conditioned medium. The dishes were incubated at 37° C. in a humidified atmosphere of 10% $CO_2$. Colonies were scored on day 12–14 after plating.

Long term marrow cultures were established and maintained essentially according to Sutherland, et al., Proc. Natl. Acad. Sci. USA 87:3584–3588 (1990). Briefly, cells were suspended in Myeloid Long-Term Culture Medium (Terry Fox Laboratory, Vancouver, B.C.) containing 12.5% horse serum, 12.5% fetal calf serum and $10^{-4}$ 2-mercaptoethanol in alpha medium supplemented with 2 mM glutamine, 0.2 mM i-inositol, 2 μM folic acid and $10^{-6}$ mol/L hydrocortisone sodium succinate. Cells were plated on pre-established, irradiated feeder layers of normal marrow. To prepare the feeder layers, allogeneic marrow was used to initiate primary LTCs in 75 mm flasks 6 weeks before the experiment. Feeder layers were maintained as described above for LTCs except that hydrocortisone was omitted from the medium after the second week to destroy hematopoietic cells, nonadherent cells were removed from the feeder layer and the adherent cells were trypsinized, irradiated with 15 Gy from a $^{60}$Co source and plated in six- or 24-well plates.

Cells sorted on the basis of Rh-123 fluorescence were plated in triplicate at $10^5$ cells per well in a six-well microtiter plate, whereas cells sorted on the basis of MRK16 reactivity were plated in duplicate at 4×$10^4$ cells per well in a 24-well plate. Cultures were maintained at 33° C., in 5% $CO_2$. At weekly intervals, one half of the nonadherent cells were removed and at the same time one half of the medium was replaced. The nonadherent cells were collected by centrifugation and assayed for short-term clonogenic cells as described above. In the experiment with cells sorted on the basis of MRK16 reactivity, all the remaining nonadherent cells were removed after 5 weeks, and cells in the adherent layer were suspended by trypsinization, washed and assayed for clonogenic cells.

We claim:

1. A method of purifying a P-glycoprotein expressing pluripotent hematopoietic stem cell from a mixture of blood or bone marrow cells, the method comprising the steps of:

(a) staining a mixture of blood or bone marrow cells with a fluorescent compound having the ability to enter cells and be retained therein, having absorbance and emission spectra suitable for fluorescence-activated cell sorting, and the ability to be a substrate for P-glycoprotein-mediated efflux, wherein the fluorescent compound is selected from the group consisting of $DiOC_2(3)$, HIDC-iodide and DODC-iodide;

(b) removing the stained cells from the fluorescent compound for a time and at a temperature sufficient to allow efflux of the fluorescent compound to produce dull and bright cells;

(c) selecting the dull cells; and (d) eliminating any T-cells present among the dull cells.

2. A method of purifying a P-glycoprotein-expressing pluripotent hematopoietic stem cell from a mixture of blood or bone marrow cells, the method comprising the steps of:

(a) incubating the mixture of cells with an antibody against P-glycoprotein to yield cells having bound antibody;

(b) purifying the cells having bound antibody by standard immunopurification techniques: and (c) eliminating any T-cells present among the antibody-bound cells.

3. A method of purifying a P-glycoprotein expressing pluripotent hematopoietic stem cell from a mixture of blood or bone marrow cells, the method comprising the steps of:
(a) staining a mixture of blood or bone marrow cells with a fluorescent compound having the ability to enter cells and be retained therein, having absorbance and emission spectra suitable for fluorescence-activated cell sorting, and the ability to be a substrate for P-glycoprotein-mediated efflux, wherein the fluorescent compound is selected from the group consisting of DiOC$_2$(3), HIDC-iodide and DODC-iodide;
(b) removing the stained cells from the fluorescent compound for a time and at a temperature sufficient to allow efflux of the fluorescent compound to produce dull and bright cells;
(c) selecting the dull cells; and
(d) selecting any CD34$^+$ cells present among the dull cells.

4. A method of purifying a P-glycoprotein expressing pluripotent hematopoietic stem cell from a mixture of blood or bone marrow cells, the method comprising the steps of:
(a) staining a mixture of blood or bone marrow cells with a fluorescent compound having the ability to enter cells and be retained therein, having absorbance and emission spectra suitable for fluorescence-activated cell sorting, and the ability to be a substrate for P-glycoprotein-mediated efflux, wherein the fluorescent compound is selected from the group consisting of DiOC$_2$(3), HIDC-iodide and DODC-iodide;
(b) removing the stained cells from the fluorescent compound for a time and at a temperature sufficient to allow efflux of the fluorescent compound to produce dull and bright cells;
(c) selecting the most dull cells.

5. A method of purifying P-glycoprotein-expressing pluripotent hematopoietic stem cells from a mixture of blood or bone marrow cells, the method comprising the steps of:
(a) incubating the mixture of cells with an antibody against P-glycoprotein to yield cells having bound antibody;
(b) purifying the cells having bound antibody by standard immunopurification techniques; and
(c) selecting any CD34$^+$ cells present among the antibody bound cells.

6. A method of purifying a P-glycoprotein expressing pluripotent hematopoietic stem cell from a mixture of blood or bone marrow cells, the method comprising the steps of:
(a) staining a mixture of blood or bone marrow cells with a fluorescent compound other than rhodamine-123, wherein the fluorescent compound has the ability to enter cells and be retained therein, has absorbance and emission spectra suitable for fluorescence-activated cell sorting, and the ability to be a substrate for P-glycoprotein-mediated efflux;
(b) removing the stained cells from the fluorescent compound for a time and at a temperature sufficient to allow efflux of the fluorescent compound to produce dull and bright cells;
(c) selecting the dull cells; and
(d) selecting any CD34$^+$ cells present among the dull cells.

7. A method of purifying a P-glycoprotein expressing pluripotent hematopoietic stem cell from a mixture of blood or bone marrow cells, the method comprising the steps of:
(a) staining a mixture of blood or bone marrow cells with a fluorescent compound other than rhodamine-123, wherein the fluorescent compound has the ability to enter cells and be retained therein, has absorbance and emission spectra suitable for fluorescence-activated cell sorting, and the ability to be a substrate for P-glycoprotein-mediated efflux;
(b) removing the stained cells from the fluorescent compound for a time and at a temperature sufficient to allow efflux of the fluorescent compound to produce dull and bright cells;
(c) selecting the dull cells; and
(d) eliminating any T-cells present among the dull cells.

8. A method of purifying a P-glycoprotein expressing pluripotent hematopoietic stem cell from a mixture of blood or bone marrow cells, the method comprising the steps of:
(a) staining a mixture of blood or bone marrow cells with a fluorescent compound other than rhodamine-123, wherein the fluorescent compound has the ability to enter cells and be retained therein, has absorbance and emission spectra suitable for fluorescence-activated cell sorting, and the ability to be a substrate for P-glycoprotein-mediated efflux;
(b) removing the stained cells from the fluorescent compound for a time and at a temperature sufficient to allow efflux of the fluorescent compound to produce dull and bright cells; and
(c) selecting the most dull cells.

* * * * *

UNITED STATES PATENT AND TRADEMARK OFFICE
CERTIFICATE OF CORRECTION

PATENT NO.  : 5,464,753
DATED       : November 7, 1995
INVENTOR(S) : Chaudhary et al.

It is certified that error appears in the above-indentified patent and that said Letters Patent is hereby corrected as shown below:

column 1, line 7 insert the following language
--The U.S. Government has a paid up license in this invention and the right in limited circumstances to require the patent owner to license others on reasonable terms as provided for by the terms of grant number CA40333 awarded by The National Institutes of Health.--

Signed and Sealed this

Sixth Day of August, 1996

Attest:

BRUCE LEHMAN

*Attesting Officer*       *Commissioner of Patents and Trademarks*